United States Patent
Wenner

(10) Patent No.: US 6,846,994 B2
(45) Date of Patent: Jan. 25, 2005

(54) SYSTEM AND METHOD TO DELAY CLOSURE OF A NORMALLY CLOSED ELECTRICAL CIRCUIT

(76) Inventor: Justin B. Wenner, 12227 Everglade St., Los Angeles, CA (US) 90066

(*) Notice: Subject to any disclaimer, the term of this patent is extended or adjusted under 35 U.S.C. 154(b) by 58 days.

(21) Appl. No.: 10/664,778

(22) Filed: Sep. 17, 2003

(65) Prior Publication Data

US 2004/0066262 A1 Apr. 8, 2004

Related U.S. Application Data

(63) Continuation-in-part of application No. 09/955,610, filed on Sep. 19, 2001, now Pat. No. 6,635,834.

(51) Int. Cl.[7] .................................................. H01H 3/16
(52) U.S. Cl. ............................ 200/61.45 M; 200/61.04; 200/61.08
(58) Field of Search ................................ 200/61.45 M, 200/61.08, 61.04, 61.03, 506, 61.06, 300

(56) References Cited

U.S. PATENT DOCUMENTS 3,868,485 A * 2/1975 Sykes et al. ............... 200/61.2
3,997,886 A * 12/1976 Lerner ........................ 137/88
4,313,042 A * 1/1982 Ehrhart .................... 200/61.04
5,846,744 A * 12/1998 Athey et al. ................ 435/7.9
6,330,465 B1 * 12/2001 Huyberechts et al. ....... 600/343

* cited by examiner

Primary Examiner—Lincoln Donovan
Assistant Examiner—K. Lee
(74) Attorney, Agent, or Firm—Rader, Fishman & Grauer PLLC

(57) ABSTRACT

A system and method are provided to delay closure of an electrical circuit of a battery-powered electrical device, intended to operate remotely in an environment in which the pH value changes from one value to another. Two electrical contacts of an electrical circuit are separated by an insulator that holds the circuit open until the device is exposed to an environment having a predetermined pH value. Exposure of the insulator to an environment having that pH value causes the insulator to dissolve and the circuit to close, energizing the device. Alternatively, A Hall effect transistor or a reed switch may be used as the switch. It is held open by the presence of a magnetic field held in place by material that is dissolvable at a predetermined pH level. When a region having that pH level is reached, the material dissolves and the circuit closes.

10 Claims, 4 Drawing Sheets

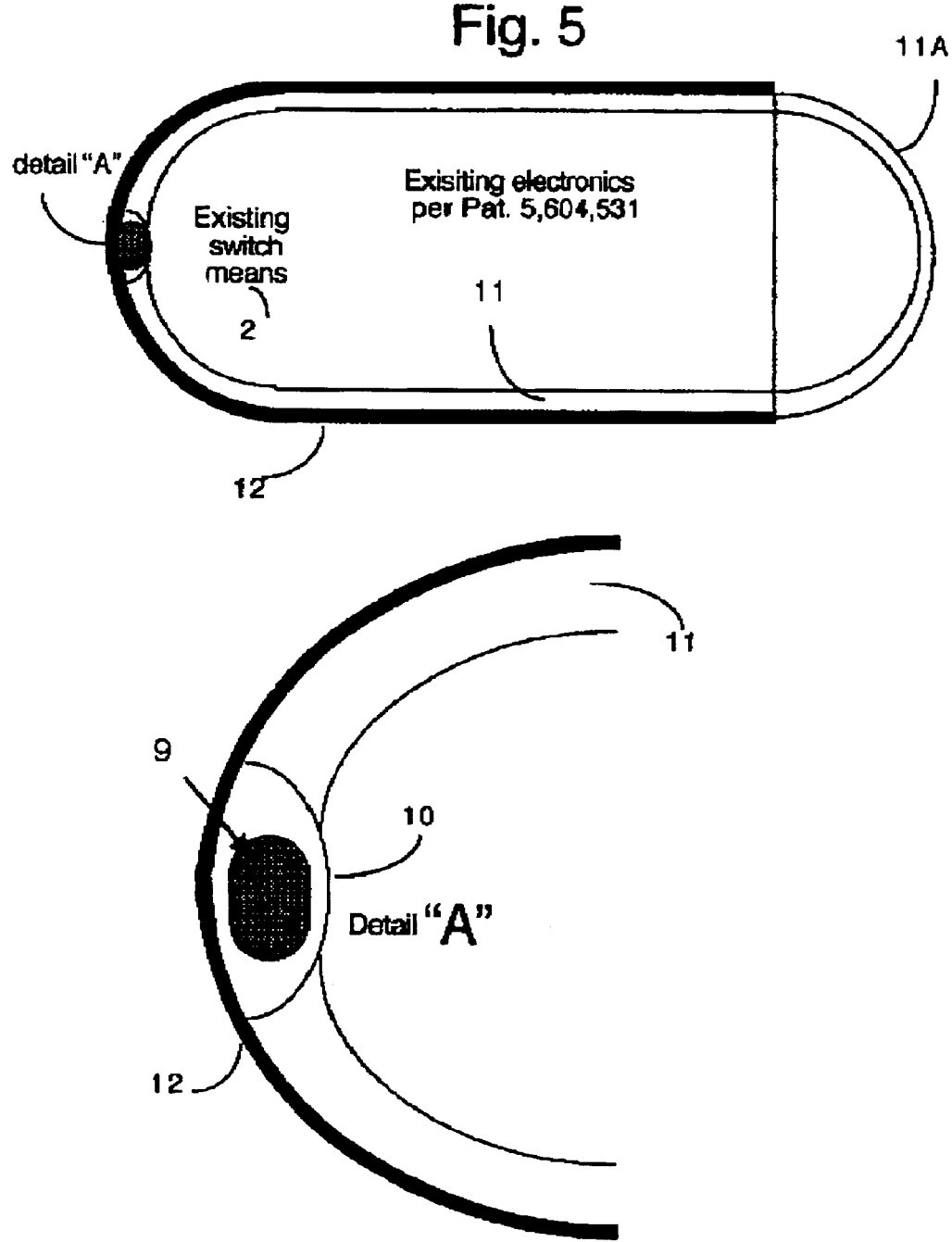

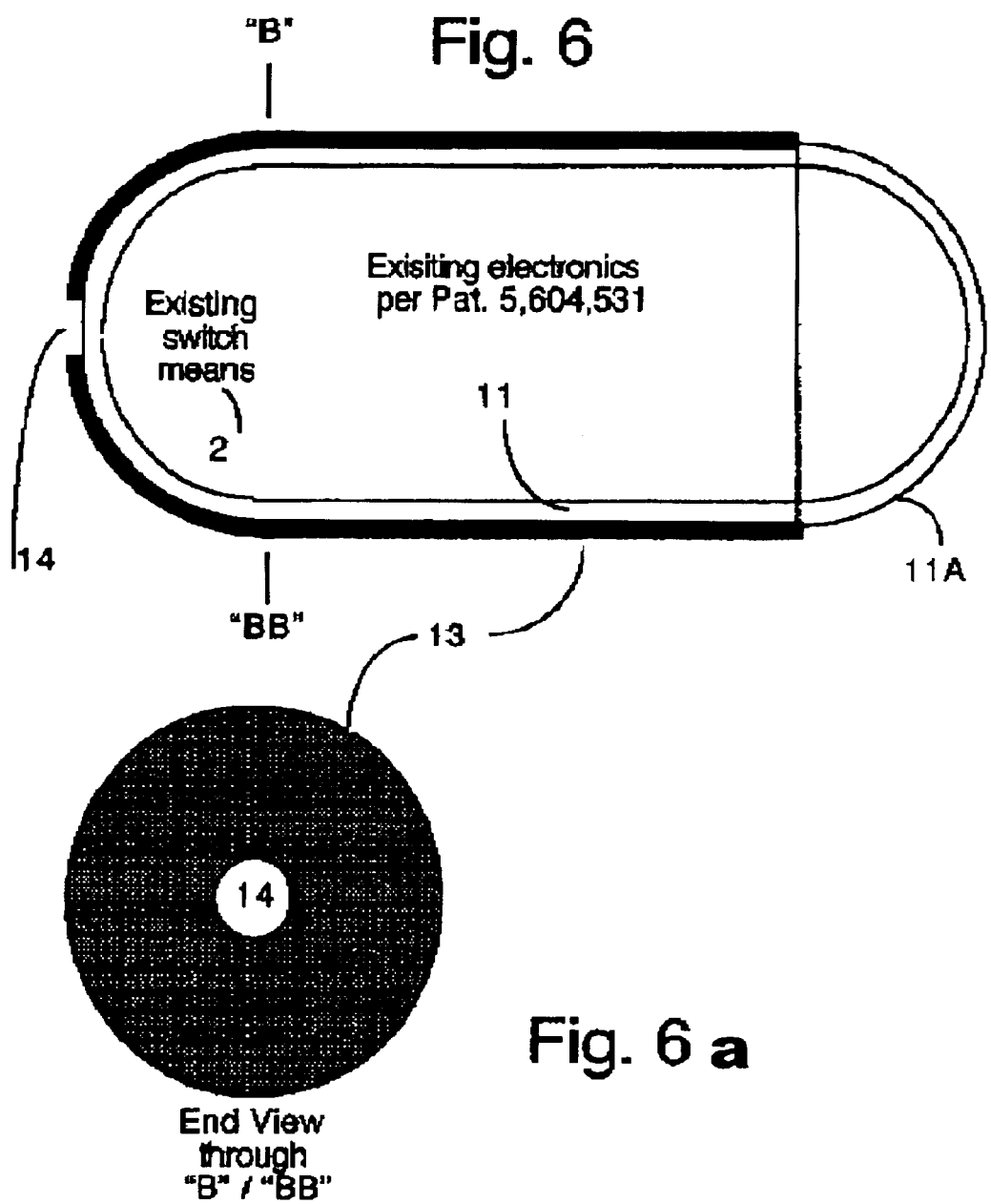

SYSTEM AND METHOD TO DELAY CLOSURE OF A NORMALLY CLOSED ELECTRICAL CIRCUIT

This is a continuation-in-part of Ser. No. 09/955,610 filed Sep. 19, 2001, now U.S. Pat. No. 6,635,834.

BACKGROUND OF THE INVENTION

This invention generally relates to delaying closure of an electrical circuit to delay activation of an electrically powered device until its activation is desired. More specifically, the present invention relates to an endoscopic camera incorporating a system for delaying electrical activation of the camera until it is properly situated for use.

Colon cancer is the second leading cause of death in humans. It is curable if it is detected early. The current method of choice for early detection of colon cancer is a colonoscopy. Unfortunately, for many, colonoscopy is an expensive and uncomfortable procedure. Also, there is a risk that the colon may be punctured during the procedure. Consequently, many people opt to avoid or postpone the procedure. As a result, thousands of people die every year because they do not get a colonoscopy.

A less intrusive and cheaper method for early detection of cancer has been developed. It is described in U.S. Pat. No. 5,604,531 to Iddan, et al., 1997 Feb. 18. In this method, a small endoscopic capsule is swallowed. The capsule contains, inter alia, a means for illumination, a video camera, a lens arrangement and a transmitter. The capsule travels through the body, taking pictures along the alimentary canal and transmitting them to a receiver attached to a belt worn by the patient. Patients are permitted to move around normally during the approximately eight hour procedure. Since the device must be small enough to be swallowed, the size of its power source, a battery, and the amount of power it can provide are severely limited. Further, the capsule must be turned on before it is swallowed. Therefore, the principal disadvantage of this device is that the power source is depleted before it completes an investigation of the small intestine and colon. Consequently, the device is unable to investigate for cancer and other abnormalities in these parts of the body. The present invention solves this problem by delaying activation of devices, such as this capsule, until needed.

There are several patents covering methods used to delay activation of electrically powered devices until they are needed. U.S. Pat. No. 5,057,824 to Stokes, 1990 Jul. 30, uses a normally closed switch held open by a removable spacer. It is designed to be used in security systems to conserve battery power until the device is ready for use. Upon manual removal of the spacer the switch closes and power is supplied. The principle disadvantage of this method is that it must be activated manually, and thus cannot be activated while in an environment that is not directly accessible, such as the human alimentary canal. If the removable spacer method were used to delay activation of the endoscopic capsule in U.S. Pat. No. 5,604,531, it would need to be activated prior to being swallowed; accordingly, the device would still run out of power prior to completing an investigation of the small intestine and colon.

U.S. Pat. No. 4,278,077 to Mizumoto, 1981 Jul. 14, uses an induction system to energize an electromagnetic field in a coil around a permanent magnet located in the device. This method energizes the device when it is needed. The principal disadvantage of this device is that it requires the patient to remain in a stationary position during the entire 8 hour process. Furthermore, this method cannot be used to energize the endoscopic capsule in U.S. Pat. No. 5,604,531 to Iddan, et al., 1997 Feb. 18, due to size constraints.

SUMMARY OF THE INVENTION

The present invention is a system and method to delay closure of an electrical circuit of a battery-powered electrical device, specifically, a swallowable endoscopic capsule, intended to operate remotely in an environment in which the pH value changes from one value to another. More specifically, a pH-sensitive material is used to hold in place the source of a magnetic field, which, in turn, holds an electrical circuit open. The magnetic field influences a switching component such as a reed switch or a magnetically controlled electrical device such as a Hall effect transistor used in conjunction with a magnet, or with a mixture of the pH-sensitive material and a magnetizable material. The magnetic field holds the electrical circuit open, or the Hall effect transistor in a non-conducting mode, until the device is exposed to an environment having a specified pH value. Exposure of the pH-sensitive material to an environment having that specified pH value causes the pH-sensitive material to dissolve. The dissolving of the material causes the switching component to close, or the Hall effect transistor to be in a conducting mode, energizing the device.

Accordingly, several objects and advantages of the invention are to provide a means to delay activation of a battery-powered device by holding it in a deactivated condition until ready for use.

An object of the present invention is to provide a means by which an electrical device can be self-activated at a specific point within an environment that is difficult to access, such as the human alimentary canal.

Another object of the present invention is to use the pH value of an environment to dissolve a pH-sensitive material separating electrical contacts to activate a battery-powered electrical device.

Still another object of the present invention is to use the pH value of an environment to dissolve a pH-sensitive material holding a magnet against a battery-powered electrical device, causing the magnet and battery-powered electrical device to separate, causing a Hall effect device to conduct, to activate a battery-powered electrical device.

Yet another object of the present invention is to use the pH value of an environment to dissolve a magnetizable coating applied to the outside of a battery-powered electrical device, said coating consisting of a mixture of a pH-sensitive material and a magnetizable material, to activate a battery-powered electrical device.

Further objects and advantages of the invention will become apparent from review of the process flow chart, drawings and description of a preferred embodiment and alternate embodiments.

BRIEF DESCRIPTION OF THE DRAWING FIGURES

The present invention will be understood more fully from the following description taken in conjunction with the drawings in which:

FIG. 5 is a schematic view of a first alternative embodiment of the endoscopic camera unit of the present invention.

FIG. 5a is an enlarged detail view of the endoscopic camera unit shown in FIG. 5.

FIG. 6 is a schematic view of a second alternative embodiment of the endoscopic camera unit of the present invention.

FIG. 6a is an end view of the endoscopic camera unit shown in FIG. 6.

DETAILED DESCRIPTION OF THE PREFERRED EMBODIMENT

This invention is primarily intended for use with a swallowable endoscopic capsule, as described in U.S. Pat. No. 5,604,531 to Iddan, et al., 1997 Feb. 18. The endoscopic capsule described in that patent is designed to take pictures of the human alimentary canal. In this prior art, the endoscopic capsule travels through the alimentary canal from the mouth to the stomach, small intestine and colon. Battery capacity is necessarily limited due to size constraints. Its batteries must be activated before it is swallowed, and the device tends to run out of battery power before reaching the colon.

The present invention delays activation of the electronic components of the endoscopic capsule device until just prior to reaching the small intestine so that it has enough remaining battery power to operate while traveling through the small intestine and the colon.

All embodiments described below use a pH-sensitive material, used either alone (as an insulating element) or in conjunction with a reed switch or a magnetically controlled electrical device such as a Hall effect transistor and a magnet or magnetizable material. The pH-sensitive material acts to hold an electrical circuit open until the device is exposed to an environment having a specified pH value. Exposure of the pH-sensitive material to an environment having that specified pH value causes the pH-sensitive material to dissolve. The dissolving of the material causes the circuit to close, or the Hall effect device to be in a conducting mode, powering the device.

All embodiments described below use a pH-sensitive material designed to dissolve when exposed to an environment having a specified pH value. The preferred material is made by Colorcon Company of West Point, Pa. 19486, described in U.S. Pat, No. 5,811,121 to Wu, et al., 1998 Sep. 22, and is under the trademark name of SURETERIC.

Figure 2:
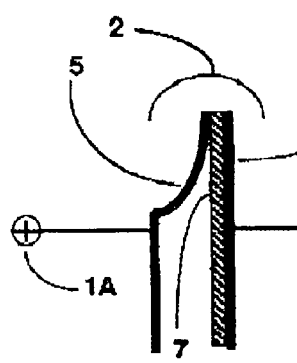
FIG. 2 shows the normally closed switch, according to the present invention, held open by the pH-sensitive material separating the contacts.

FIG. 2 shows the preferred embodiment having a normally closed switch connected in series between the battery and electrical circuitry of a swallowable endoscopic capsule and held open by a pH-sensitive insulating element 7. The normally closed switch 2 has a movable contact 5 and a stationary contact 6. Pursuant to the preferred embodiment of the present invention, the stationary contact 6 is coated with a pH-sensitive element 7 designed to dissolve when exposed to an environment having a specified pH value. The material 7 holds the movable contact 5 separate from the stationary contact 6, keeping the battery 1 and battery-powered electrical device 3 inactive. The preferred material 7 is made by Colorcon Company of West Point, Pa. 19486, described in U.S. Pat. No. 5,811,121 to Wu, et al., 1998 Sep. 22, and is under the trademark name of SURETERIC. Color may be added to the material 7 to allow for easy identification of differing pH values. The movable contact 5 and stationary contact 6 may be made of various materials, including, but not limited to, brass, copper and phosphor bronze.

Figure 1:
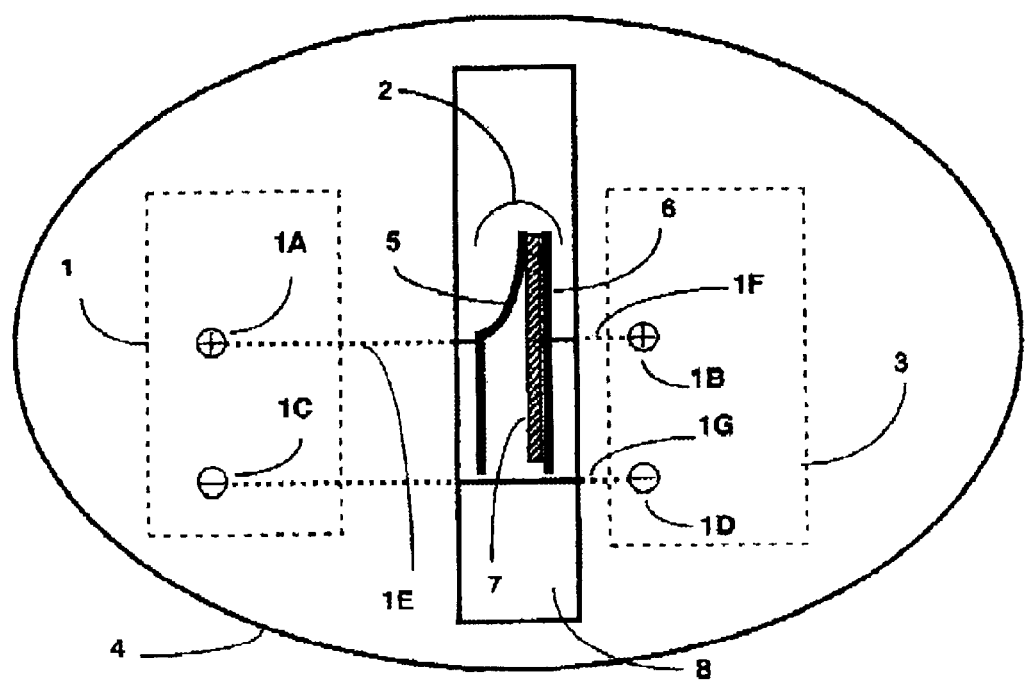
FIG. 1 shows the normally closed switch, according to the present invention, held open by a pH-sensitive material and connected in series between the battery and electrical circuitry of a swallowable endoscopic capsule.

As shown in FIG. 1, the protective covering 4 of the endoscopic capsule contains an opening 8, allowing the material 7 coated on the stationary contact 6 to be exposed directly to the various environments of the alimentary canal as the capsule travels from the mouth through the stomach, small intestine and colon. Each region through which the capsule travels, during at least part of its journey, has an ever-increasing pH value, starting with a value of pH 1–2 in the stomach and finally reaching a value above pH 7 in the colon. The material 7 that holds the switch 2 open will dissolve upon reaching a region in which the pH value is greater than that of the material 7. For example, if the stationary contact 6 is coated with a material with a pH of 4, it will dissolve after leaving the stomach and before reaching the colon. Once the material 7 is dissolved, the switch 2 will close, causing the battery 1 to provide power to electrically powered device 3.

FIG. 1 shows a battery 1 inside protective cover 4, which contains opening 8. Opening 8 exposes to the outside environment only that section of the capsule containing the switch. It is unnecessary, and may be undesirable, to expose the other capsule components. Positive electrode 1A of battery 1 is connected to movable contact 5 of a normally closed switch 2 by wire 1E, and stationary contact 6 of switch 2 is connected to the positive lead 1B of electrically powered device 3 by wire 1F. Negative electrode 1C of battery 1 is connected to the negative lead 1D of 3 by wire 1G.

As shown in FIG. 2, switch 2, which is normally biasis toward its closed position, has movable contact 5 which is held apart from stationary contact 6 by insulating material 7 that is designed to dissolve at a specified pH value. The material 7 prevents electrical current from flowing from positive electrode 1A to positive lead 1B.

Figure 3:
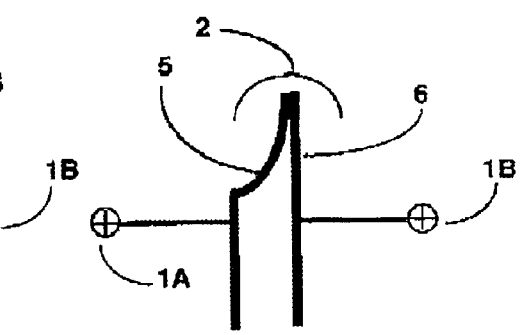
FIG. 3 shows the normally closed switch, according to the present invention, after the pH-sensitive material has dissolved.

FIG. 3 shows a normally closed switch 2 after the material 7, shown in FIG. 2, dissolves. Accordingly, FIG. 3 shows a normally closed switch 2 with movable contact 5 closed against stationary contact 6, allowing current to flow from positive electrode 1A to positive lead 1B.

Figure 4:
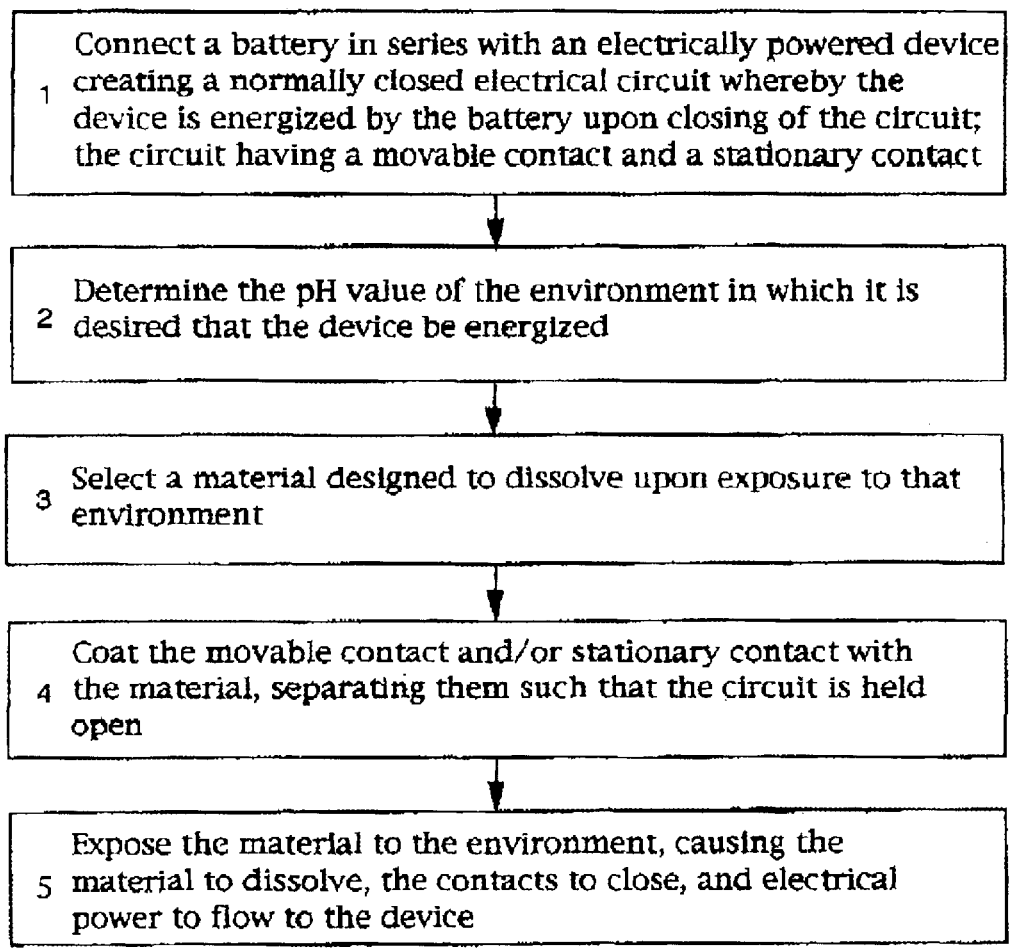
FIG. 4 is a process flow chart for the preferred embodiment of the present invention.

FIG. 4 is a process flow chart for the preferred embodiment of the present invention. At step 1, a battery is connected in series with an electrically powered device, creating a normally closed electrical circuit whereby the device is energized by the battery upon closing of the circuit. The circuit has a movable contact and stationary contact. At step 2, the pH value of the environment in which it is desired that the device be energized is determined. At step 3, a material designed to dissolve upon exposure to that environment is selected. At step 4, either the movable contact and/or stationary contact is coated with the material, separating them such that the circuit is held open. Finally, at step 5, the material is exposed to the desired environment, causing the material to dissolve, the contacts to close, and electrical power to flow to the device.

As an alternative embodiment, the pH-sensitive insulating material is applied directly to the positive and/or negative ends of at least one battery within the circuit. The material holds the circuit open until the material dissolves. When the material dissolves, a movable contact holding the battery in place closes against the battery, allowing current to flow.

In two alternative embodiments, the switch means utilized to complete the circuit and power the capsule's components is a Hall effect transistor or similar circuitry such as a reed switch. The Hall effect transistor is operable to open the capsule's electrical circuit when it is in the presence of a magnetic field, and to close the capsule's electrical circuit (thus powering the capsule's camera and transmitter components) when the magnetic field is absent. A reed switch consists of two magnetic contacts in a tube. When a magnet is close to a reed switch, the two contacts become magnetized and repel each other, blocking electrical current. When the magnet is moved away from the reed switch the contacts demagnetize and move to their original, closed position.

In one alternative embodiment schematically shown in FIGS. 5 and 5a, small magnet 9 is held in dimple 10 in the end of the endoscopic capsule. The capsule is then coated with the pH-sensitive material, holding the magnet in place against the capsule. The magnet's magnetic field holds a Hall effect transistor inside the capsule a non-conducting mode. Exposure of the material to an environment having a specified pH value causes the pH-sensitive material to dissolve, causing the magnet and capsule to separate, causing said Hall effect transistor to conduct, energizing said capsule.

In another alternative embodiment schematically shown in FIGS. 6 and 6a, the pH-sensitive material is mixed with a magnetizable material, such as an iron powder, creating a magnetizable coating. The coating is applied to the outside of the swallowable endoscopic capsule. When the coating is magnetized, the resulting magnetic field maintained between opposite poles at central opening 14 and distal opening 16 holds a Hall effect transistor in a non-conducting mode. Exposure of the coating to an environment having a specified pH value causes the pH-sensitive material to dissolve, destroying the magnetic field. The destruction of the magnetic field causes the Hall effect transistor to conduct, thus activating the camera and transmitter circuitry in the swallowable endoscopic capsule.

The embodiment schematically depicted in FIG. 5 utilizes a magnetic field to hold the electrical switch means in a non-conducting mode until the magnetic field is destroyed. FIG. 5 shows some, but not all, of the components of an endoscopic capsule: a shell 11, shell cap 11A, and an electrical switch means 2. In this embodiment, magnet 9 is placed in a dimple 10 at the end of shell 11. A coating 12 is applied to both the magnet 9 and the outside of shell 11, such that when coating 12 dries and hardens, magnet 9 is held in place in dimple 10 at the end of shell 11. The preferred magnet is a rare earth magnet. The preferred coating is the pH-sensitive material described above. Alternatively, magnet 9 can be coated in place against the end of shell 11 without the need for a dimple. The magnet 9 will hold an electrical switch means 2, which is part of the electrical circuit of the endoscopic capsule, in a non-conducting mode. The preferred switch means is either a Hall effect device or some other normally closed switch means. Exposure of the coating to an environment having a specified pH value causes the coating to dissolve, and causes the magnet to separate from the shell. This separation removes the capsule from the magnetic field, allowing the Hall effect device to conduct, thus activating the electronics of the endoscopic capsule where needed.

FIG. 6 shows another alternative embodiment. Similar to the second alternative embodiment described above, this embodiment also utilizes a magnetic field to hold the electrical switch means in a non-conducting mode until the magnetic field is destroyed. The main difference is that, rather than using a discrete magnet, this embodiment employs a magnetizable coating 13 on the outside of shell 11 of the endoscopic capsule. The preferred coating 13 is a mixture of the pH-sensitive material, described above, and a powdered magnetizable material. The preferred magnetizable material is powdered iron, powdered rare earth or powdered Alnico. Coating 13 is magnetizable.

Coating 13 is applied to the outside of the shell 11. The area of the coating at the end of the shell 11 has an opening 14 to focus the magnetic field. It is preferable that the shell 11 be coated prior to placing any electronics inside the shell. After coating 13 is applied to the shell 11, the coating 13 is magnetized. When magnetized, said coating 13 will hold an electrical switch means, which is part of the electrical circuit of the swallowable endoscopic capsule, in a non-conducting mode. Exposure of the coating 13 to an environment having a specified pH value causes the material to dissolve, which allows the magnetic field formed by the coating 13 to be destroyed, allowing the Hall effect transistor to conduct, or the said switch means to close, thus activating the electronics of the endoscopic capsule where needed. As an example, the electronics of the endoscopic capsule can be activated in the stomach, intestine, colon, or other environment along the alimentary canal, based on the predetermined pH level at which the coating is set to dissolve.

FIG. 7 is a process flow chart describing the third alternative embodiment for the present invention. At step 1, the pH value of the environment in which it is desired that the electronic device be activated is determined. At step 2, a material designed to dissolve upon exposure to said environment is selected. At step 3, a powdered magnetizable material is selected. At step 4, said powdered magnetizable material and said pH-sensitive material are mixed. At step 5, the mixture is applied to the outside of an endoscopic capsule shell, and is allowed to dry, forming a coating. At step 6, said coating is magnetized. At step 7, the electronics and other components of the endoscopic capsule are inserted into the shell, and the shell cap is attached to the shell, and the capsule is sealed closed. At step 8, the coated endoscopic capsule is exposed to an environment having the pH value determined in step 1 above, causing the coating to dissolve, destroying the magnetic field, and thereby allowing electrical power to flow, activating the electrical device.

From the above, it should be understood that the embodiments described, in regard to the drawings, are merely exemplary and that a person skilled in the art may make variations and modifications to the shown embodiments without departing from the spirit and scope of the invention. All such variations and modifications are intended to be included within the scope of the invention as defined by the appended claims. This information is meant to be illustrative and not limiting.

I claim:

1. A system for delaying activation of a battery-powered electrical device, intended to operate remotely in an environment in which a pH value changes from a first value to a second value, comprising:

a housing defining an interior space and having an exterior surface;

a magnetic field source proximally associated with said housing, said magnetic field source being separable from said housing upon exposure to an environment having a pH value equal to said second value;

a normally closed electrical circuit disposed in said housing; said circuit having a battery connected in series with an electrically powered device, whereby said electrically powered device is powered by said battery upon closing of said circuit;

said circuit having switch means sensitive to the presence of a magnetic field associated with said magnetic field source; said switch means operable to open said circuit in the presence of said magnetic field and to close said circuit in the absence of said magnetic field;

whereby when said housing encounters an environment having a pH value equal to said second value, said magnetic field source separates from said housing and said circuit closes, powering said electrically powered device.

2. A system for delaying activation of a battery-powered electrical device, as in claim 1, wherein said magnetic field source is fixed to said exterior surface by a coating which is dissolvable upon exposure to an environment having a pH value equal to said second value.

3. A system for delaying activation of a battery-powered electrical device, as in claim 2, wherein said magnetic field source comprises a magnet fixed to said exterior surface by said coating.

4. A system for delaying activation of a battery-powered electrical device, as in claim 3, wherein said magnet is disposed in a dimple defined in said exterior surface.

5. A system for delaying activation of a battery-powered electrical device, as in claim 2, wherein said coating comprises a mixture of pH-sensitive material and magnetizable material, which mixture may be magnetized.

6. A system for delaying activation of a battery-powered electrical device, as in claim 1, wherein said switch means comprises a reed switch biased open, but closed when influenced by said magnetic field.

7. A system for delaying activation of a battery-powered electrical device, as in claim 1, wherein said switch means comprises a Hall effect device, said magnetic field holding said Hall effect device in a non-conducting mode, so that when said magnetic field is separated from said housing, said Hall effect device transition to a conducting mode, thereby closing the circuit and powering the electrically powered device.

8. A system for delaying activation of a battery-powered electrical device, as in claim 7, wherein said Hall effect device is a hall effect transistor.

9. A system for delaying activation of a battery-powered electrical device, as in claim 1, wherein said housing is a swallowable capsule.

10. A system for delaying activation of a battery-powered electrical device, as in claim 1, wherein said electrical device includes a video camera.

* * * * *